United States Patent [19]

Brunelli

[11] 4,167,942

[45] Sep. 18, 1979

[54] HOT COMPRESS APPLICATOR

[76] Inventor: Angelo J. Brunelli, 128 Phillips, Niles, Ohio 44446

[21] Appl. No.: 834,839

[22] Filed: Sep. 19, 1977

[51] Int. Cl.$^2$ .................................................. A61F 7/00

[52] U.S. Cl. .................................................. 128/254

[58] Field of Search ......................... 128/254, 256, 380

[56] References Cited

U.S. PATENT DOCUMENTS

| | | | |
|---|---|---|---|
| 1,825,118 | 9/1931 | Jaeg | 128/256 X |
| 3,195,539 | 7/1965 | Hyman | 128/256 |

*Primary Examiner*—John D. Yasko

*Attorney, Agent, or Firm*—Webster B. Harpman

[57] ABSTRACT

A hot compress applicator for the symptomatic treatment of the eye comprising an insulated receptacle for liquid, a portion of which has a gauze pad covered eye cup in communication with the liquid receptacle by way of a metering aperture. In use the receptacle is filled with hot water and held so as to place the gauze pad against the eye allowing a measured amount of water to be absorbed by the gauze pad.

6 Claims, 3 Drawing Figures

HOT COMPRESS APPLICATOR

BACKGROUND OF THE INVENTION (1) Field of the Invention

This invention relates to eye hot compress applicators of the type normally employed to supply moist heat to the eye area of the user.

(2) Description of the Prior Art

Prior structures of this type have utilized liquid reservoirs for supplying hot or cold water to eye pads. For example see U.S. Pat. Nos. 2,313,282 and 3,195,539.

U.S. Pat. No. 2,313,282 discloses a pair of reservoirs with eye conforming sponge rubber pads attached thereto which are capable of absorbing the entire volume of ice and water supplied within the reservoirs. In the present invention a single reservoir supplies a measured amount of hot water to a gauze pad covered eye cup upon demand.

U.S. Pat. No. 3,195,539 discloses a water reservoir having an electric immersion heater adjacent a porous heat shield and a sponge pad for engagement against the eye, so as the water is heated, steam and hot water flow through the porous shield and into the sponge pad at a constant and unmetered rate.

In the present invention a reservoir is filled with hot water which is dispensed as needed in a measured amount to a gauze pad by inverting the reservoir to alternately allow air and water to flow through the metering aperture.

SUMMARY OF THE INVENTION

A hot compress applicator comprising an eye cup covered with a gauze pad that conforms to the shape of the eye area and an insulated liquid reservoir is in communication with the eye cup by way of a metering aperture which on demand allows a measured amount of hot water to be released to the eye cup and absorbed by the gauze pad.

DESCRIPTION OF THE PREFERRED EMBODIMENT

Figure 1:
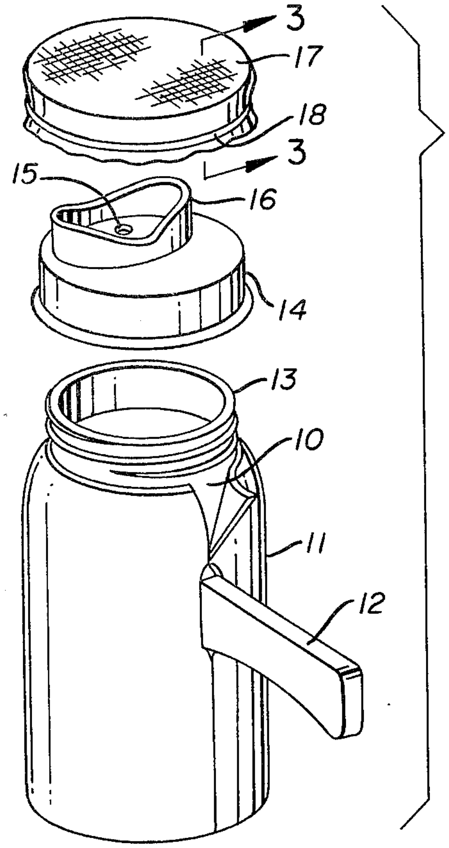
FIG. 1 is an exploded view of the hot compress applicator.
Figure 2:
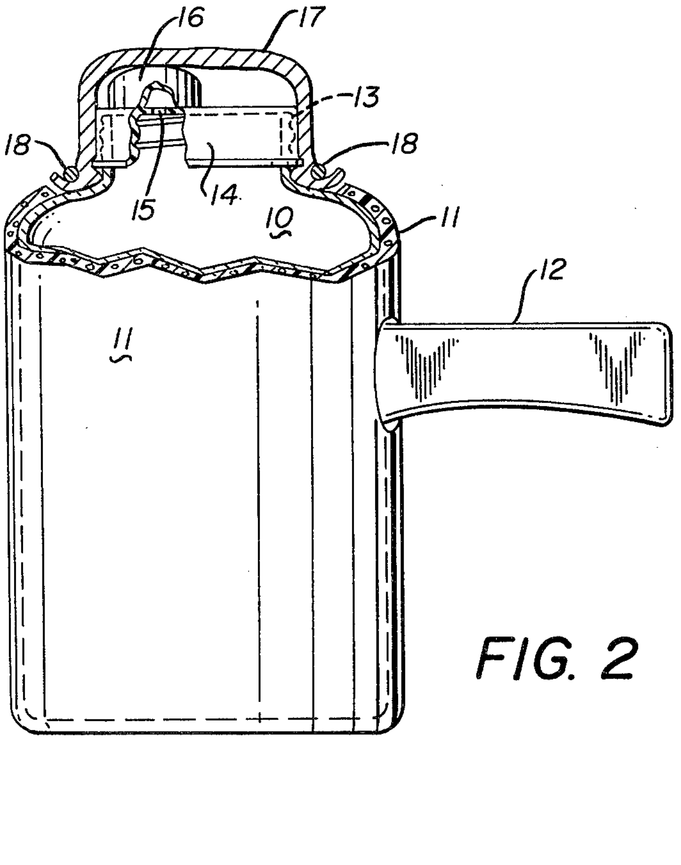
FIG. 2 is a side view with parts broken away and parts in cross section.

In it simplest form as seen in FIGS. 1 and 2 of the drawings, the hot compress applicator comprises a reservoir such as a bottle 10 having an insulated jacket 11 thereabout and a handle 12 attached thereto. The neck of the bottle 10 has an external spiral thread pattern 13 formed thereon for the reception of an internally threaded closure 14 such as illustrated in FIG. 2 of the drawings.

Figure 3:
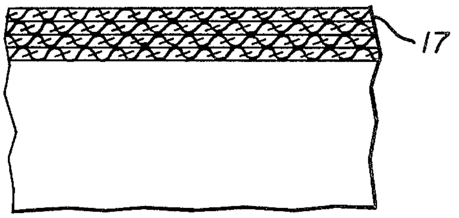
FIG. 3 is an enlarged cross section on line 3—3 of FIG. 1.

By referring now to FIG. 1 of the drawings, it will be seen that the closure 14 has a metering aperture 15 therein and an elliptical shaped eye cup 16 thereon so as to be positioned around the aperture 15. A gauze pad 17 is fastened over the eye cup 16 and the enclosure 14 and removably attached thereto by an elastic band 18 or the like. The elastic band 18 holds the peripheral edge of the gauze pad 17 in secured position against the neck of the bottle 10 and inunder the edge of the closure 14 as best seen in FIG. 2 of the drawings. An enlarged cross section of a portion of the gauze pad 17 is illustrated in FIG. 3 of the drawings.

In use the insulated bottle 10 is filled with hot water, the closure 14 is attached thereto and the gauze pad 17 is positioned thereover along with the elastic band 18. The bottle 10 is then inverted and a predetermined amount of hot water flows through the metering aperture 15 to moisten the gauze pad 17 in the area of the eye cup 16. A partial vacuum is formed within the bottle 10 which prevents additional flow of hot water through the metering aperture 15. By alternating inverting the hot compress applicator, the user can maintain the desired temperature and moisture in the gauze pad 17.

Although but one embodiment of the present invention has been illustrated and described, it will be apparent to those skilled in the art that various changes and modifications may be made therein without departing from the spirit of the invention and having thus described my invention, what I claim is:

1. A hot compress applicator for the eye comprising a container defining a liquid reservoir and having a neck portion with a fastening configuration, a removable cap therefor having a registering configuration, said cap having a small aperture therein, a replaceable gauze pad positioned over said removable cap and means on said cap spacing a portion of said gauze pad with respect to said aperture, said means comprising an upstanding flange positioned around said aperture and being larger in area than said eye, and means for detachably holding said gauze pad over said cap and said upstanding flange.

2. The hot compress applicator of claim 1 and wherein said container is a bottle with the neck portion having the fastening configuration and the means spacing the gauze pad from the aperture is an upstanding flange of irregular shape.

3. The hot compress applicator of claim 1 and wherein said upstanding flange is shaped to form an eye cup.

4. The hot compress applicator of claim 1 and wherein the means for detachably holding the gauze pad comprises an elastic band.

5. The hot compress applicator of claim 1 and wherein an insulating jacket encloses the and a handle extends perpendicularly from a surface of said container on a plane parallel to and spaced with respect to said apertured cap.

6. The hot compress applicator of claim 4 and wherein the exterior configurations of the container and removable cap are arranged to form an area of reduced diameter therebetween for receiving said means for detachably holding said gauze pad.

* * * * *